United States Patent [19]
Clausen et al.

[11] Patent Number: 4,936,759
[45] Date of Patent: Jun. 26, 1990

[54] BLOOD RESERVOIR/PUMP

[75] Inventors: Earl W. Clausen, Eden Prairie; Lloyd C. Hubbard, Deephaven, both of Minn.

[73] Assignee: Minnesota Mining and Manufacturing Company, St. Paul, Minn.

[21] Appl. No.: 300,265

[22] Filed: Jan. 23, 1989

[51] Int. Cl.⁵ .............................................. F04B 35/04
[52] U.S. Cl. .............................. 417/423.14; 417/423.9; 128/DIG. 3
[58] Field of Search ............. 417/423.15, 423.1, 423.9, 417/423.14, 424, 423.3, 420, 423.11, 423.6; 416/177, 189, 193 R; 415/DIG. 4, 206, 203, 56.2; 128/DIG. 3; 604/151

[56] References Cited
U.S. PATENT DOCUMENTS

| | | | |
|---|---|---|---|
| 1,712,012 | 5/1929 | Traudt | 417/361 |
| 2,304,289 | 12/1942 | Ruthman | 417/361 |
| 2,933,045 | 4/1960 | Isserlis | 417/56.2 |
| 4,350,646 | 9/1982 | Baus | 417/420 |

Primary Examiner—Leonard E. Smith
Assistant Examiner—Robert N. Blackmon
Attorney, Agent, or Firm—Donald M. Sell; Walter N. Kirn; Robert W. Hoke, II

[57] ABSTRACT

A combined blood reservoir/pump for heart/lung bypass surgery includes a chamber having an upper reservoir chamber and a lower pump chamber with a passage connecting the reservoir chamber and the pump chamber. An inlet positioned adjacent an upper end of the housing supplies blood to the reservoir. An impeller is positioned in the pump chamber and is driven by a shaft which has its lower end connected to the impeller and an upper end connected to a drive motor which is mounted near the top end of the housing. An outlet is connected to the pump chamber for supplying blood from the combination blood reservoir/pump.

23 Claims, 5 Drawing Sheets

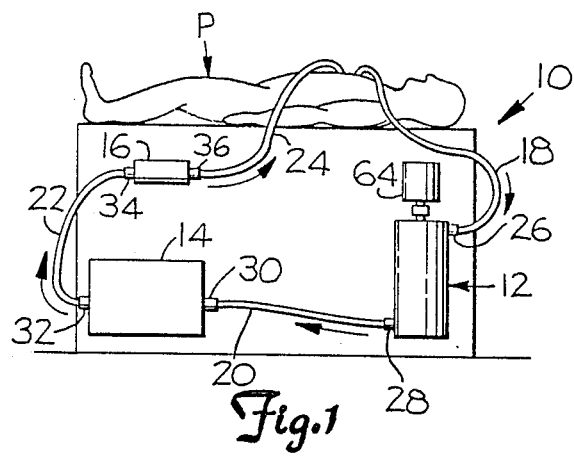
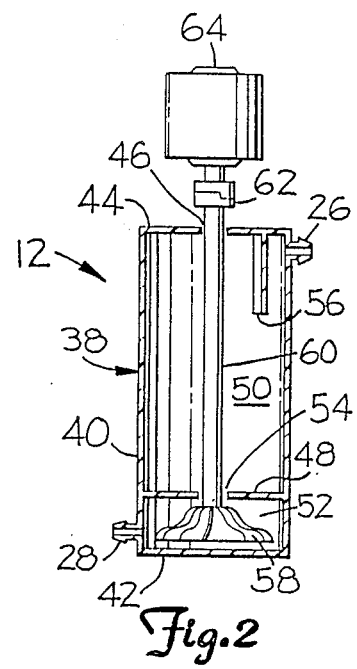
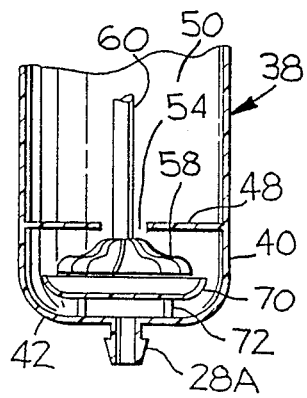
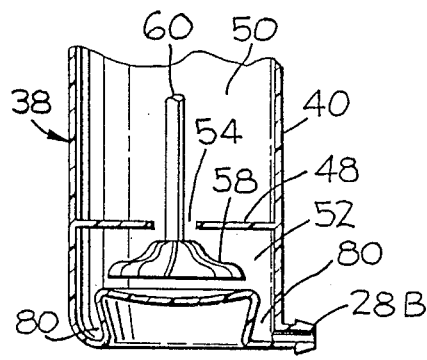

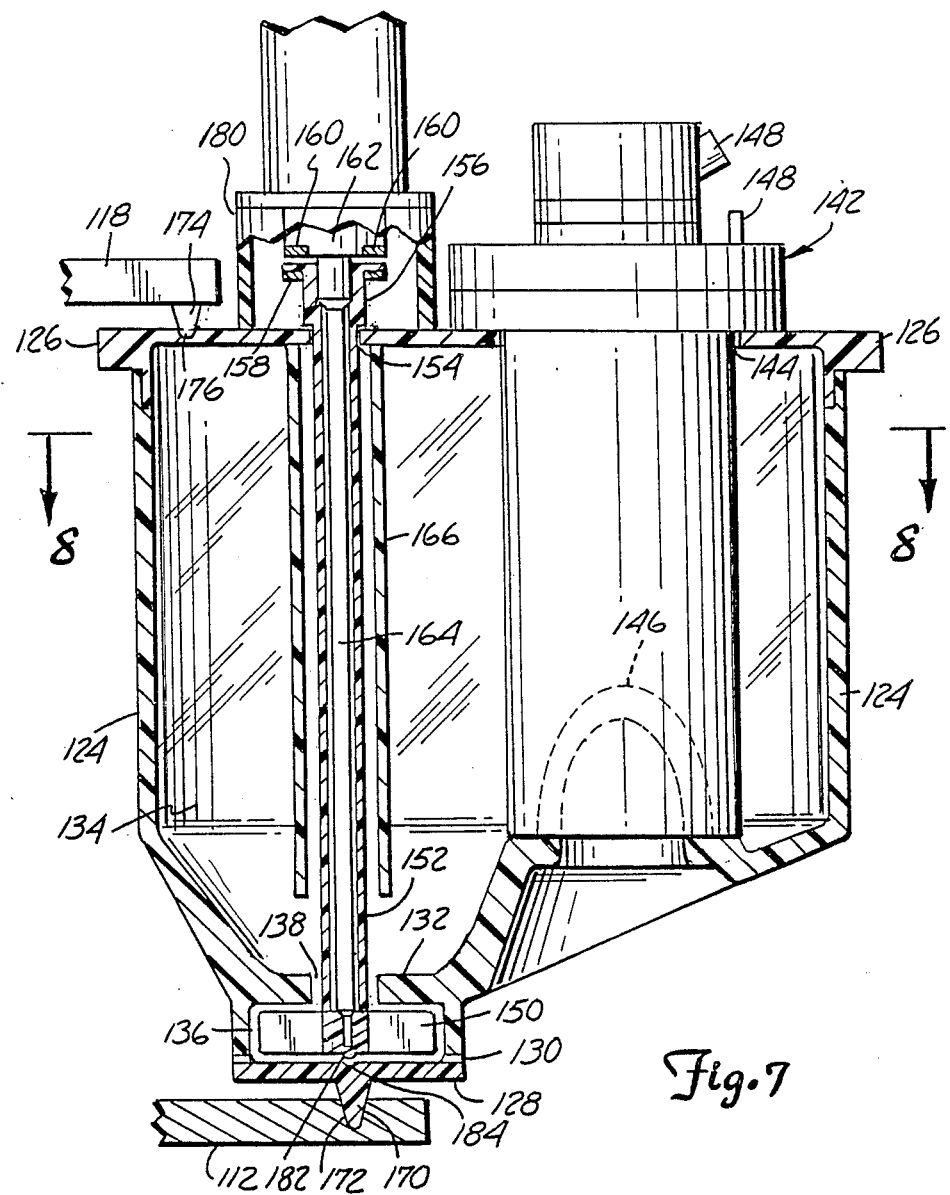

4,936,759

BLOOD RESERVOIR/PUMP

BACKGROUND OF THE INVENTION

1. Field of the Invention

The present invention relates to apparatus for storing and pumping blood during surgery. In particular, the present invention relates to a combination centrifugal pump and blood reservoir.

2. Description of the Prior Art

In a surgical procedure for repair of heart defects, the patient's heart must usually be stopped to facilitate the delicate surgical process. To sustain life during this process, tubes are surgically introduced into the major veins (vena cavae) and artery (aorta) which conduct blood to and from the heart. This blood is diverted from the vein to a heart/lung machine (which includes a blood pump, a reservoir, and an artificial lung) and is reintroduced into the aorta.

A major concern for the heart surgical team is to prevent the inadvertent introduction of air into the heart/lung machine. The introduction of an air embolus into the patient's circulation can cause serious injury or death. The use of a centrifugal blood pump (as opposed to a peristaltic or roller pump) has been increasing in recent years because, among other reasons, of the ability of the centrifugal pump to prevent the introduction of a large bolus of air into the patient. Similarly, use of a collapsible or soft reservoir bag rather than a rigid reservoir has increased because, by collapsing when empty, the soft reservoir bag presents a barrier to the introduction of air.

SUMMARY OF THE INVENTION

The present invention is a combination blood reservoir/pump which combines a centrifugal pump and a blood reservoir in a single unit. The reservoir/pump includes a housing having an upper reservoir chamber and a lower pump chamber, with a blood flow passage between the two chambers which functions as an outlet for the reservoir chamber and an inlet for the pump chamber. An impeller, driven by a drive motor located outside the pump/reservoir, is positioned within the pump chamber.

A reservoir inlet to the reservoir/pump is positioned adjacent an upper end of the housing and is in communication with the reservoir chamber. In preferred embodiments, a baffle is positioned within the housing to prevent the formation of a vortex by the blood within the reservoir chamber.

A pump outlet is connected to the pump chamber. In some preferred embodiments, lateral forces on the impeller are minimized by providing a circumferential opening which communicates with the pump outlet and which is positioned to collect the blood outflow and to stop the rotation of the blood, thereby converting velocity into pressure as the velocity of the blood decreases upon entering the outlet port.

BRIEF DESCRIPTION OF THE DRAWINGS

FIG. 1 is a diagram which displays schematically a heart/lung bypass system including the blood reservoir/pump of the present invention.

FIG. 2 is a sectional view showing one preferred embodiment of the reservoir/pump of the present invention.

FIGS. 3 and 4 are partial sectional views showing two embodiments of the reservoir/pump of the present invention utilizing circumferential outlet ports to reduce lateral deflection of the impeller and shaft within the pump chamber.

FIG. 7 a sectional view along section 7—7 of FIG. 6.

DETAILED DESCRIPTION OF THE PREFERRED EMBODIMENTS

Figure 5:
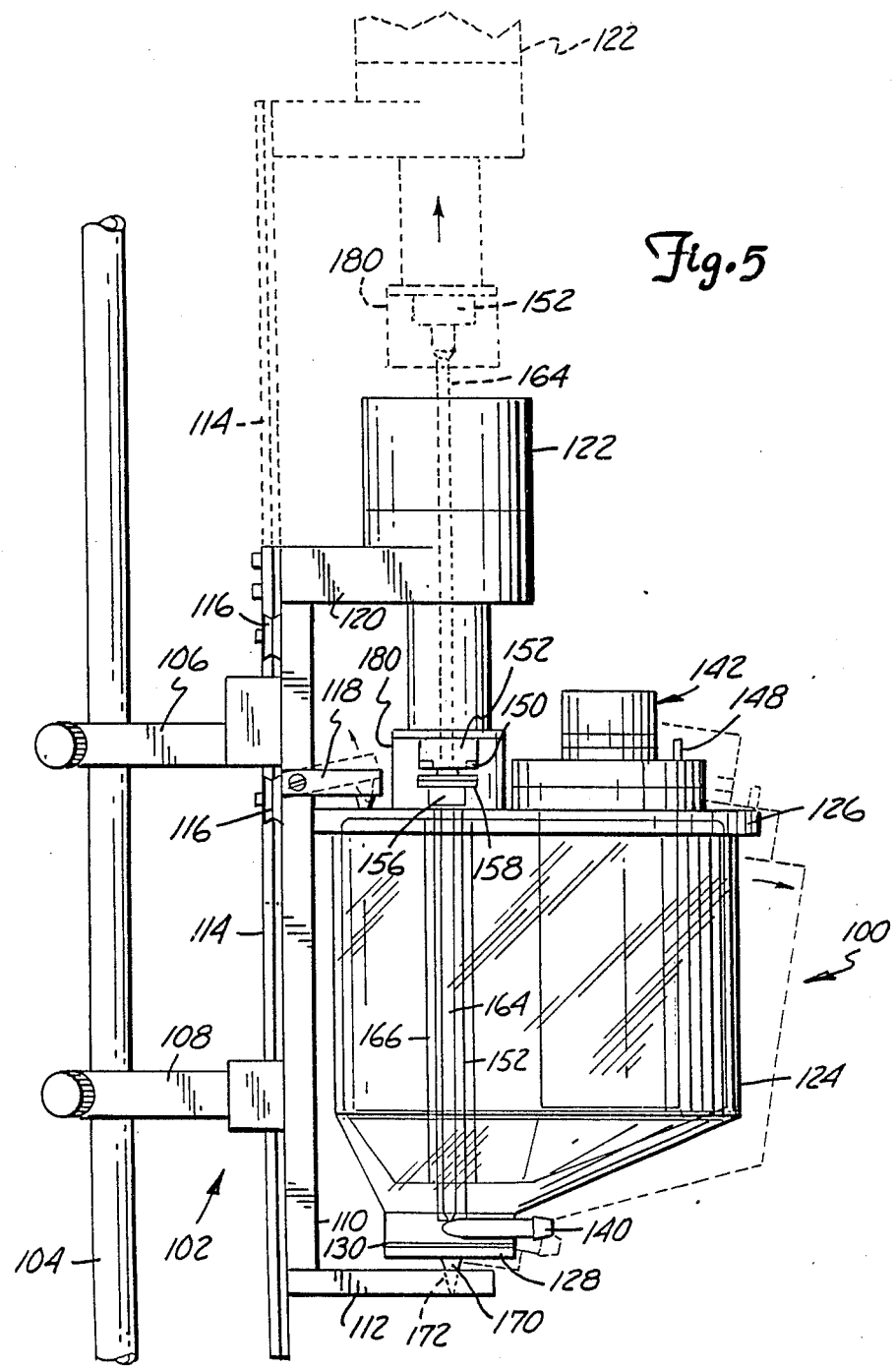
FIG. 5 is a side view of another embodiment of the reservoir/pump of the present invention.

FIG. 1 shows heart/lung bypass system 10 be used during heart surgery on patient P. System 10 includes reservoir/pump unit 12 of present invention, oxygenator 14, filter 16 and tubing 18, 20, 22, and 24. Tubing 18 has one end introduced into a major vein (vena cavae) of patient P, and its other end connected to reservoir inlet 26 of reservoir/pump unit 12. Tubing 20 connects pump outlet 28 of reservoir/pump unit 12 to inlet 30 of oxygenator 14. Tubing 22 is connected between outlet 32 of oxygenator 14 and inlet 34 of filter 16. Tubing 24 is connected between outlet 36 of filter 16 and the aorta of patient P.

As illustrated by the arrows in FIG. 1, blood is diverted from the vena cavae of patient P through tubing 18 to reservoir/pump unit 12, and is supplied through tubing 20 to oxygenator 14. Oxygenated blood from oxygenator 14 is supplied through filter 16 to the aorta of patient P. System 10 replaces the heart and lungs of the patient P during open heart surgery or other surgical procedures where heart/lung functions must be stopped or are inadequate to sustain the patient.

FIG. 2 shows reservoir/pump unit 12 in greater detail. In this embodiment, reservoir/pump unit 12 includes housing 38, which has generally cylindrical side walls 40, a closed bottom 42, and a generally closed top 44 with a central opening 46.

Interior wall 48, which is positioned near the lower end of housing 38, divides the interior of housing 38 into an upper reservoir chamber 50 and a lower centrifugal pump chamber 52. Pump inlet 54 in wall 48 provides communication between the lower end of reservoir chamber 50 and the upper end of pump chamber 52.

Reservoir inlet 26 is positioned near the upper end of housing 38, and supplies blood from tubing 18 into reservoir chamber 50. Baffle 56 is positioned adjacent reservoir inlet 26 within reservoir chamber 50 to prevent formation of a vortex by the incoming blood. A vortex, if formed, could cause air to enter pump chamber 52 before reservoir chamber 50 was completely empty.

Positioned within pump chamber 52 is pump impeller 58, which is attached to the lower end of pump shaft 60. Pump shaft 60 extends upward from pump impeller 58 through pump inlet 54, through reservoir chamber 50, and out top 44 of housing 38 through central opening 46. Pump shaft 60 is connected through coupler 62 to electric drive motor 64. Rotational force is supplied from electric motor 64 through coupler 62 and shaft 60 to cause rotation of pump impeller 58. The rotation of pump impeller 58 draws fluid through pump inlet 54 and out through pump outlet 28.

After it has been used, reservoir/pump unit 12 is discarded. This is typical of other prior art reservoirs and pumps used in open heart surgery. An important advantage of the present invention, however, is that there are no seals required between drive motor 64, shaft 60, and the remainder of reservoir/pump unit 12. In contrast, in other prior art centrifugal blood pumps, it has been necessary to provide bearings to support the rotating impeller, and to provide some form of rotating shaft seal between the blood chamber and the drive mechanism chamber of the pumps to prevent contamination of the bearings by blood.

Reservoir/pump unit 12 shown in FIG. 2 requires no seal because of the use of pump shaft 60, which extends from outside of the reservoir/pump housing 38 and downward into pump chamber 52. Impeller 58 relies on the bearings of motor 64 for positioning. Since motor 64 never comes in contact with the blood, it can be reused; and therefore the bearings are not discarded along with reservoir/pump unit 12 as has been typical with prior art centrifugal blood pumps.

In the embodiment shown in FIG. 2, pump outlet 28 is positioned in side wall 40 of housing 38. Because blood exits pump chamber 52 in FIG. 2 from one side, this can cause an unbalanced lateral force to be directed against impeller 58. Shaft 60, therefore, must be sufficiently stiff so that this lateral force does not cause sufficient deflection of impeller 58 and shaft 60 to affect operation of reservoir/pump unit 12.

FIGS. 3 and 4 show alternative embodiments of the present invention, which permit a less stiff pump shaft 60 to be used. In FIG. 3, pump outlet 28A is positioned in bottom wall 42, and is generally axially aligned with pump shaft 60. Pump outlet baffle 70 is supported by pump outlet baffle support post 72 below impeller 58. Pump outlet baffle 70 and side and bottom walls 40 and 42 define a circumferential collector gap for collecting the blood outflow and stopping the rotation of the blood. This converts velocity into pressure according to the formula $P + \frac{1}{2}\rho V^2 = K$, where P is pressure, $\rho$ is fluid density, V is velocity, and K is a constant. Therefore, as the fluid velocity decreases on entering outlet port 28A, fluid pressure increases. The use of a circumferential collector gap, as defined by pump outlet baffle 70, balances the lateral forces, so that the net force in the lateral direction on impeller 58 is zero.

FIG. 4 shows another embodiment in which a circumferential channel collector 80 communicates with the lower and outer periphery of pump chamber 52. As in the embodiment shown in FIG. 3, the blood is collected uniformly around the outer periphery of the pump chamber 58 by collector 80 and is slowed down to convert velocity into outlet pressure at pump outlet 28B. Once again, the lateral forces on impeller 58 are balanced, so that shaft deflection is not produced.

FIGS. 5-9 show another embodiment of the present invention. Disposable reservoir/pump unit 100 is supported by support assembly 102, which in turn is attached to mast 104 of a heart/lung machine. Support assembly 102 includes a pair of support arms 106 and 108 which extend outward from mast 104. Attached to arms 106 and 108 is vertical mount 110, which supports bottom support plate 112, movable slide 114, slide guides 116, pivotable arm 118, and motor support arm 120. Drive motor 122 is attached to the outer end of support arm 120.

Reservoir pump unit 100 includes main housing section 124 (which is preferably a clear plastic material so that the level of blood can be easily observed), top cover 126, and bottom 128. Main housing 124 and bottom 128 preferably are connected together by adhesive bonding layer 130, although other means for making a fluid tight connection (such as a mating threads) can also be used.

As best shown in FIG. 7, the interior of main housing of 124 is divided by interior wall 132 into reservoir chamber 134 and pump chamber 136. Pump chamber 136 communicates with reservoir chamber 134 through pump inlet opening 138 in interior wall 132. Blood exits pump chamber through pump outlet 140 (FIG. 5).

Mounted on top 126 is filter assembly 142, which, in preferred embodiments, is a conventional filter used in heart/lung systems. The lower portion of filter assembly 142 extends through hole 144 in top 126 and into reservoir chamber 134. Projection 146 of housing 124 helps to locate the lower portion of filter assembly 142 within reservoir chamber 134.

Blood is received through blood inlets 148 of filter assembly 142. In preferred embodiments, one of the blood inlets 148 is connected through a tube to the patient to receive venous blood. Other blood inlets 148 are connected to cardiotomy suction (to receive suctioned blood from the patient's chest cavity), to an oxygenator shunt recirculation line, and to medication and priming lines.

The fluid received through inlets 148 passes through filter assembly 142 and into blood reservoir chamber 134. The fluid flow path is then through pump inlet opening 138 into pump chamber 136. Fluid is pumped out of pump chamber 136 through pump outlet 140.

Positioned within pump chamber 136 is impeller 150. Tubular drive shaft 152 is connected at its lower end to impeller 150 and extends upward through opening 138, through reservoir chamber 134, and through opening 154 in top 126. At the upper end of drive shaft 152 is shaft coupling head 156, which carries ferromagnetic coupling 158. Magnets 160 carried at the lower end of motor shaft 162 attract coupling 158 so that impeller 150 is rotated by motor 122 through motor shaft 162, coupling 158, and drive shaft 152.

Attached to motor shaft 162 is metal alignment shaft 164 which extends downward through drive shaft 152 to impeller 150. Alignment shaft 164 does not itself drive impeller 150, but rather ensures that necessary strengthing precision is achieved.

Because of the construction of the reservoir/pump of the present invention, it is necessary that drive shaft 152 (together with alignment shaft 164) have three important characteristics. First, it must be stiff enough to prevent deflection under high flow conditions. Second, it must be precise enough to locate the rotating impeller 150 in the center of pump chamber 136. Third, it must be small enough in diameter to avoid causing turbulence and foaming at the interface of blood and air within reservoir chamber 134. All three of these properties must be satisfied, while still providing a low cost, disposable reservoir/pump unit.

In the embodiment shown in FIGS. 5-9, these necessary characteristics are achieved. Alignment shaft 164 is a precision metal shaft, and is reusable because it is shielded from contact with blood by tubular drive shaft 152. It is the shaft tip of alignment shaft 164 at the lower end which positions impeller 150 to the required precision. Drive shaft 152 does not have to be precision molded and, in fact, can be made of commercially available tubing stock. This helps to maintain a low cost for the entire disposable reservoir pump unit 100.

Surrounding drive shaft 152 is baffle 166, which prevents the rotation of drive shaft 152 from creating a vortex within reservoir chamber 134. This avoids the possibility of a vortex drawing air into pump chamber 136. In this embodiment, baffle 166 is a sleeve attached to the underside of top 126 and extending downward to a position near interior wall 132.

Reservoir/pump unit 100 is disposable—i.e. it is used for only a single patient. Unit 100 is positioned on support plate 112 by boss 170, which engages detents 172 in plate 112. Unit 100 is held in place by pivotable arm 118, which has downwardly extending bosses 174 which engage detents 176 on top 126. To remove reservoir/pump unit 100, motor 122 is moved vertically upward via slide mechanism 114 to the raised position shown in phantom in FIG. 5. In the raised position, alignment shaft 164 is fully withdrawn from drive shaft 152. By pivoting arm 118 to the position shown in phantom in FIG. 5, unit 100 can be tipped outward and removed as is also shown in phantom in FIG. 5.

Figure 6:
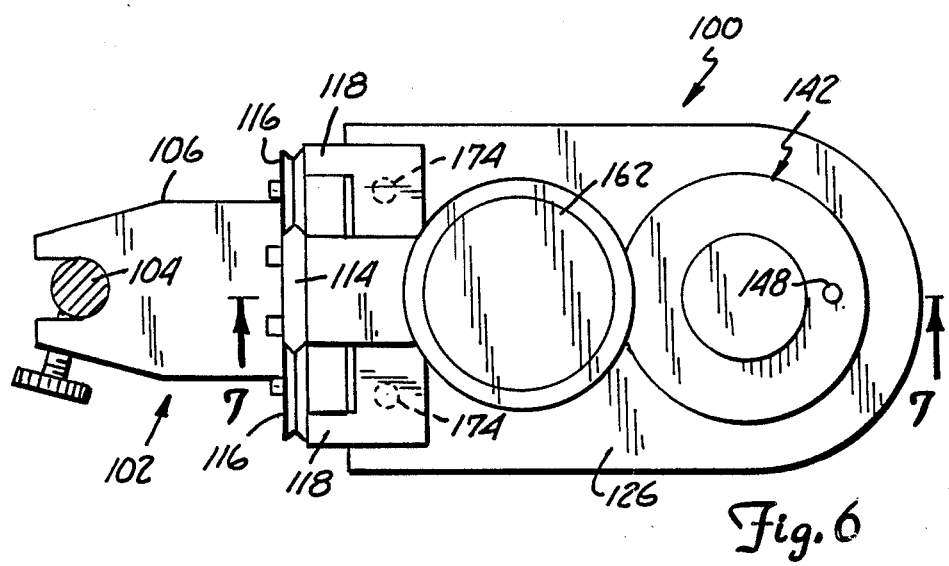
FIG. 6 is a top view of the reservoir/pump of FIG. 5.
Figure 8:
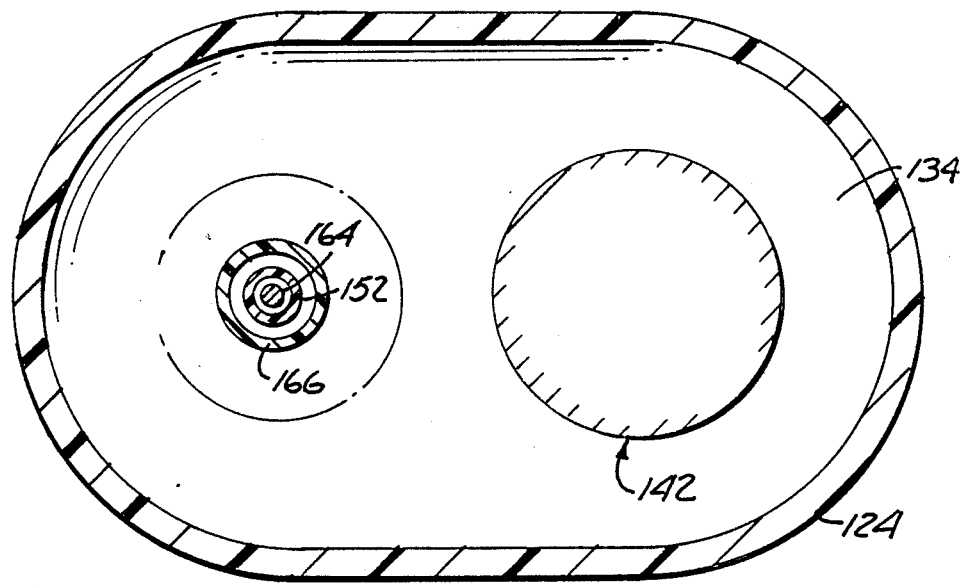
FIG. 8 is a sectional view along section 8—8 of FIG. 7.
Figure 9:
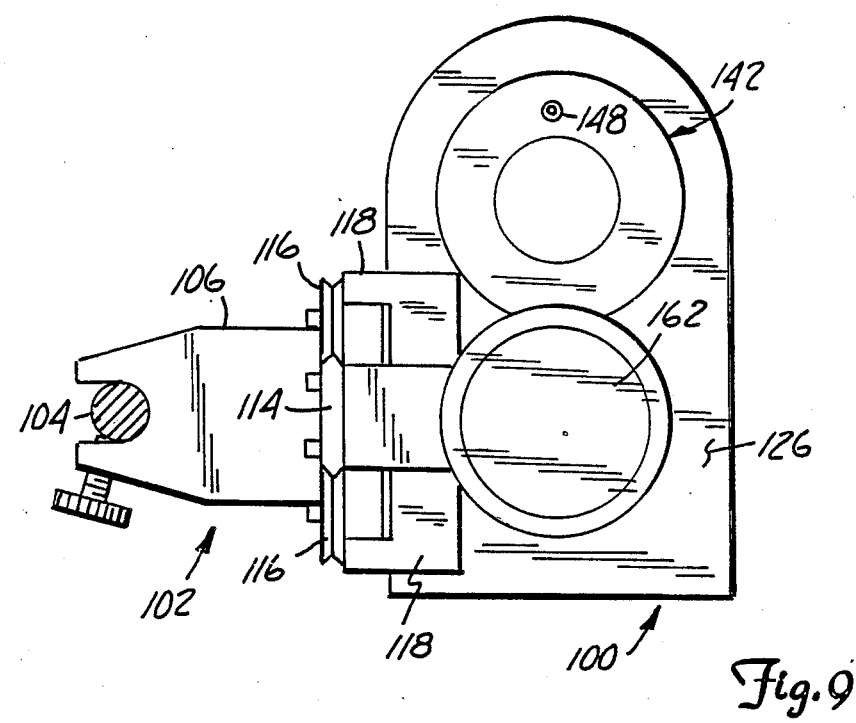
FIG. 9 is a top view showing the reservoir pump in an alternative orientation.

The opposite process is used when inserting a new unit 100 into position. Boss 170 is inserted into detent 172 of support plate 112 and unit 100 is pivoted into position while arm 118 is pivoted upward. Arm 118 is then allowed to lower until bosses 174 engage detents 176 in top 126. In a preferred embodiment, there are two possible orientations of unit 100, as illustrated by FIGS. 6 and 9, and two sets of detents 176 are provided in top 126.

Motor 122 is then lowered so that alignment shaft 164 extend downward through drive shaft 152. The downward movement of motor 122 is limited by locating cup 180, which surrounds the lower end of drive shaft 162 and which engages top 126 of unit 100 when motor 122 has reached its lower point of movement. At this lower end point, magnets 160 are close enough to coupling 158 to attract coupling 158. This lifts impeller 150 off from bottom 128 to the generally centered position illustrated in FIG. 7. Prior to being lifted, impeller 150 is located within pump chamber 136 against bottom 128, with projection 182 resting in detent 184. This establishes a predictable location for impeller 150 to ensure proper insertion of alignment shaft 164.

In conclusion, the present invention provides a rigid reservoir and centrifugal pump for heart surgery which is simple in construction, and which can be manufactured for a cost which is a little more than the cost of a reservoir alone. The danger of air emboli which can result in a rigid reservoir is virtually eliminated by the use of a centrifugal pump in conjunction with the reservoir and within the same housing. The elimination of the bearings and the seal of the centrifugal pump also greatly increases the reliability of the pump, while reducing the cost.

Although the present invention has been described with reference to preferred embodiments, workers skilled in the art will recognize that changes may be made in form and detail without departing from the spirit and scope of the invention.

What is claimed is:

1. A blood reservoir/pump for use with a drive motor, the blood reservoir/pump comprising:
   a housing having a reservoir chamber and a pump chamber connected by a passage between a lower end of the reservoir chamber and an upper end of the pump chamber, the pump chamber being positioned generally below the reservoir chamber;
   a reservoir inlet in communication with the reservoir chamber;
   a pump outlet in communication with the pump chamber;
   an impeller positioned in the pump chamber;
   means for coupling the impeller to the drive motor to cause rotation of the impeller within the pump chamber; and
   means positioned in the reservoir chamber for preventing formation of a vortex in blood within the reservoir chamber.

2. The blood reservoir/pump of claim 1 wherein the means for preventing formation of a vortex comprises a baffle positioned within the reservoir chamber.

3. The blood reservoir/pump of claim 1 and further comprising:
   circumferential collecting means positioned adjacent a periphery of the pump chamber for collecting blood and supplying the blood to the pump outlet.

4. The blood reservoir/pump of claim 3 wherein the circumferential collecting means comprises:
   outlet baffle means positioned adjacent and spaced from side and bottom walls of the pump chamber for defining a blood collecting gap which is connected to the pump outlet.

5. The blood reservoir/pump of claim 1 wherein the housing comprises:
   a top;
   a bottom;
   a side wall between the top and bottom defining a generally closed interior; and
   an interior wall positioned within the interior for separating the interior into the reservoir chamber and the pump chamber, the interior wall having the passage therein.

6. The blood reservoir/pump of claim 5 wherein the interior wall is generally parallel to the bottom.

7. The blood reservoir/pump of claim 5 wherein the interior wall is positioned more closely to the bottom than to the top.

8. The blood reservoir/pump of claim 1 and further comprising:
   filter means positioned in the reservoir chamber for filtering blood received at the reservoir inlet.

9. The blood reservoir/pump of claim 1 wherein the means for coupling comprises:
   a shaft having a lower end and an upper end, the shaft extending downward through the reservoir chamber, through the passage and into the pump chamber, with its lower end connected to the impeller; and
   means for connecting the upper end of the shaft to the drive motor.

10. The blood reservoir/pump of claim 9 wherein the shaft comprises
    a hollow tube having the impeller connected at a lower end and the means for connecting connected at an upper end; and
    an alignment shaft which extends through substantially an entire length of the hollow tube.

11. The blood reservoir/pump of claim 10 wherein the means for preventing formation of a vortex comprises a sleeve positioned around the shaft.

12. The blood reservoir/pump of claim 9 and further comprising:
    housing support means for supporting the housing; and
    drive motor support means for supporting the drive motor above the housing.

13. The blood/reservoir pump of claim 12 wherein the drive motor support means and the housing support means are movable relative to one another along a movable slide to permit insertion and removal of the housing from the housing support means.

14. The blood/reservoir pump of claim 13 wherein the housing support means includes:
   a lower support on which the housing is supported; and
   an upper support for engaging an upper portion of the housing to hold the housing in position on the lower support.

15. The blood/reservoir pump of claim 14 wherein the upper support is movable between a first position in which it is in engagement with the upper portion of the housing and a second position in which it is out of engagement.

16. The blood/reservoir pump of claim 15 wherein the upper support is pivotable between the first and second positions.

17. The blood reservoir pump of claim 16 wherein the upper support and the housing include cooperating means for defining a positional relationship of the housing with respect to the housing support means.

18. The blood/reservoir pump of claim 14 wherein the lower support includes a detent for receiving a mating projection from the housing.

19. The blood/reservoir pump of claim 1 and further comprising:
   a lower support on which the housing is supported; and
   an upper support for engaging an upper portion of the housing to hold the housing in position on the lower support.

20. The blood/reservoir pump of claim 19 wherein the upper support is movable between a first position, in which it is in engagement with the upper portion of the housing and a second position in which it is out of engagement.

21. The blood/reservoir pump of claim 20 wherein the upper support is pivotable between the first and second positions.

22. The blood/reservoir pump of claim 19 wherein the upper support and the housing include cooperating means for defining a positioned relationship of the housing with respect to the upper support.

23. The blood/reservoir pump of claim 19 wherein the lower support includes a detent for receiving a mating projection from the housing.

* * * * *